United States Patent [19]

Ju

[11] Patent Number: 5,876,936
[45] Date of Patent: Mar. 2, 1999

[54] NUCLEIC ACID SEQUENCING WITH SOLID PHASE CAPTURABLE TERMINATORS

[75] Inventor: Jingyue Ju, Redwood City, Calif.

[73] Assignee: Incyte Pharmaceuticals, Inc., Palo Alto, Calif.

[21] Appl. No.: 786,838

[22] Filed: Jan. 15, 1997

[51] Int. Cl.$^6$ .............................. C12Q 1/68; C12P 19/34
[52] U.S. Cl. .......................... 435/6; 435/91.1; 536/23.1; 536/25.3
[58] Field of Search .............................. 435/6, 91.1, 810; 536/23.1, 25.3

[56] References Cited

U.S. PATENT DOCUMENTS

| | | | |
|---|---|---|---|
| 5,401,632 | 3/1995 | Wang et al. | 435/6 |
| 5,405,746 | 4/1995 | Uhlen | 435/6 |
| 5,484,701 | 1/1996 | Cocuzza et al. | 435/6 |
| 5,518,900 | 5/1996 | Nikiforov et al. | 435/91.1 |
| 5,573,913 | 11/1996 | Rosemeyer et al. | 435/6 |
| 5,610,287 | 3/1997 | Nikiforov et al. | 536/24.3 |

OTHER PUBLICATIONS

Ikeda et al., DNA Res. 2(5), 225–227 (1995).
Ansorge, W., et al., (1987) "Automated DNA sequencing: ultrasensitive detection of fluorescent bands during electrophoresis," *Nucl. Acids Res.*, 15 (11): 4593–4602.
Beck, S., et al., (1989) "Chemiluminescent detection of DNA: application for DNA sequencing and hybridization," *Nucl. Acids Res.* 17(13): 5115–5123.
Beck, S., (1990) "Colorimeteric–Detected DNA Sequencing," *Meth. in Enzymology* 184: 612–617.
Griffin, H.G., et al., (1993) "DNA Sequencing—Recent Innovations and Future Trends," *Appl. Biochem. and Biotech.* 38:147–159.
Ju, J. et al. (1996) "Energy transfer primers: A new fluorescence labeling paradigm for DNA sequencing and analysis," *Nature Medicine*, 2 (2): 246–249.

Livak, K.J., et al., (1992) "Detection of single base differences using biotinylated nucleotides with very long linker arms," *Nucl. Acid Res.* 20(18): 4831–4837.
McGuigan, et al., (1993) "DNA Fingerprinting by Sampled Sequencing," *Methods in Enzymology* 218:241–257.
Perkin Elmer (1990) "Guide to Interpretation of 373A Dye Primer and Dye Terminator Data," *User Bulletin* Model 373A DNA Sequencing System, 17:1–6.
Richterich, P., (1989) "Non–radioactive chemical sequencing of biotin labelled DNA," *Nucl. Acids Res.*, 17:(6):2181–2186.
Roskey, M.T., et al., (1996) "DNA sequencing by delayed extraction–matrix–assisted laser desorption/ionization time of light mass spectrometry," *Proc. Natl. Acad. Sci. USA* 93: 4724–4729.
Seliger, H., et al., (1990) "New Methods for the Solid–Phase Sequence Analysis of Nucleic Acid Fragments Using the Sanger Dideoxy Procedure," *Nucleosides & Nucleotides*, 9 (3): 383–388.
Stahl, S., et al., (1988) "Solid phase DNA sequencing using the biotin–avidin system," *Nucl. Acids Res.* 16(7): 3025–3038.
Tong, X., et al., (1992) "Solid–Phase Method for the Purification of DNA Sequencing Reactions," *Anal. Chem.* 64: 2672–2677.

(List continued on next page.)

*Primary Examiner*—Kenneth R. Horlick
*Attorney, Agent, or Firm*—Bret E. Field; Bozicevic & Reed LLP

[57] ABSTRACT

Methods of enzymatic nucleic acid sequencing are provided in which solid-phase capturable chain terminators are employed. In the subject methods, sequencing fragments are generated, where the fragments comprise capturable chain terminators. The fragments are then captured on a solid phase and separated from the remaining components of the sequencing reaction. The fragments are then released from the solid phase, size separated and detected to yield sequencing data from which the sequence of the nucleic acid is determined.

34 Claims, 8 Drawing Sheets

OTHER PUBLICATIONS

Tong, X., et al., (1993), "Solid phase purification in automated DNA sequencing," *DNA Sequence—J.DNA Sequencing and Mapping,* 4, 151–162.

Wahlberg, J., et al., (1990), "General colorimetric method for DNA diagnostics allowing direct solid–phase genomic sequencing of the positive samples," *Proc. Natl. Acad. Sci. USA* 87:6569–6573.

Wahlberg, J., et al., (1990), "Rapid detection and sequencing of specific in vitro amplified DNA sequences using solid phase methods," *Mol. and Cell. Probes* 4: 285–297.

Wahlberg, J., et al., (1992), "Automated magnetic preparation of DNA templates for solid phase sequencing," *Electrophoresis* 13:547–551.

Yu, H., et al., (1995), "A Comparative Study of PCR Product Detection and Quantitation by Electro–chemiluminescence and Fluorescence," *J. Biolumin Chemilumin* 10: 239–245.

NUCLEIC ACID SEQUENCING WITH SOLID PHASE CAPTURABLE TERMINATORS

TECHNICAL FIELD

The field of the this invention is nucleic acid sequencing.

BACKGROUND OF THE INVENTION

Methods of determining the sequence of nucleic acids are some of the most important tools in the field of molecular biology. Since the development of the first methods of DNA sequencing in the 1970s, sequencing methods have progressed to the point where a majority of the operations are now automated, thus making possible the large scale sequencing of whole genomes, including the human genome. There are two broad classes of DNA sequencing methodologies: (1) the chemical degradation or Maxam & Gilbert method and (2) the enzymatic or dideoxy chain termination method (also known as the Sanger method), of which the latter is the more commonly used and is suitable for automation.

Of particular interest in DNA sequencing are methods of automated sequencing, in which fluorescent labels are employed to label the size separated fragments or primer extension products of the enzymatic method. Currently, three different methods are used for automated DNA sequencing. In the first method, the DNA fragments are labeled with one fluorophore and then run in adjacent sequencing lanes, one lane for each base. See Ansorge et al., Nucleic Acids Res. (1987)15: 4593–4602. In the second methods, the DNA fragments are labeled with oligonucleotide primers tagged with four fluorophores and all of the fragments are run in one lane. See Smith et al., Nature (1986) 321: 674–679. In the third method, each of the different chain terminating dideoxynucleotides is labeled with a different fluorophore and all of the fragments are run in one lane. See Prober et al., Science (1987) 238: 336–341. The first method has the potential problems of lane-to-lane variations as well as a low throughput. The second and third methods require that the four dyes be well excited by one laser source, and that they have distinctly different emission spectra. Otherwise, multiple lasers have to be used, increasing the complexity and the cost of the detection instrument.

With the development of Energy Transfer primers which offer strong fluorescent signals upon excitation at a common wavelength, the second method produces robust sequencing data in currently commercial available sequencers. However, even with the use of Energy Transfer primers, the second method is not entirely satisfactory. In the second method, all of the false terminated or false stop fragments are detected resulting in high backgrounds. Furthermore, with the second method it is difficult to obtain accurate sequences for DNA templates with long repetitive sequences. See Robbins et al., Biotechniques (1996) 20: 862–868.

The third method has the advantage of only detecting DNA fragments incorporated with a terminator. Therefore, backgrounds caused by the detection of false stops are not detected. However, the fluorescence signals offered by the dye-labeled terminators are not very bright and it is still tedious to completely clear up the excess of dye-terminators even with AmpliTaq DNA Polymerase (FS enzyme). Furthermore, non-sequencing fragments are detected, which contributes to background signal. Applied Biosystems Model 373 A DNA Sequencing System User Bulletin, November 17,P3, August 1990.

Thus, there is a need for the development of improved methodology which is capable of providing for highly accurate sequencing data, even for long repetitive sequences. Such methodology would ideally include a means for isolating the DNA sequencing fragments from the remaining components of the sequencing reaction mixtures such as salts, enzymes, excess primers, template and the like, as well as false stopped sequencing fragments and non-sequencing fragments resulting from contaminated RNA and nicked DNA templates.

Relevant Literature

Methods of DNA sequencing are reviewed in Griffin and Griffin, Applied Biochemistry and Biotechnology (1993) 38: 147–159.

The effect of different labeling methodologies in automated DNA sequencing is discussed in Perkin Elmer User Bulletin (August 1990, Number 17) entitled "guide to Interpretation of 373A Dye Primer and Dye Terminator Data.

The use of biotinylated nucleotides in various sequencing applications is described in U.S. Pat. Nos. 5,484,701; 5,405, 746 and 5,401,632, as well as in the following literature references: Yu et al., J. Biolumin. Chemilumin. (1995) 10: 239–245; Tong & Smith, J. DNA Sequencing and Mapping (1993) 4: 151–162; Wahlberg et al., Electrophoresis (1992) 13: 547–551; Tong & Smith, Anal. Chem. (1992) 64:2672–2677; Livak et al., Nuc. Acids. Res. (1992) 18: 4831–4837; Wahlberg et al., Molecular and Cellular Probes (1990) 4: 285–297; Wahlberg et al., Proc. Natl. Acad. Sci. USA (1990) 87: 6569–6573; Seliger et al., Nucleosides and Nucleotides (1990) 9:383–388; Beck, Methods of Enzymology (1990) 184: 612–617; Richterich, Nuc. Acids Res. (1989) 17:2181–2186; Beck et al., Nuc. Acids Res. (1989) 17: 5115–5123; Stahl et al., Nuc. Acids. Res. (1988) 16: 3025–3038.

SUMMARY OF THE INVENTION

Methods of determining the sequence of a nucleic acid through enzymatic sequencing are provided. In the subject methods, capturable chain terminators are employed to produce primer extension products, usually labeled primer extension products, which are capable of being captured on a solid-phase. The primer extension products are then isolated through capture on a solid-phase, released from the solid phase, size separated and detected to yield sequencing data from which the nucleic acid sequence is determined. In one preferred embodiment, the primers employed to generate the primer extension products are labeled with fluorescent energy transfer fluorescent labels that are excited at a common wavelength but provide a distinguishable fluorescent signal associated with each of the four chain terminating bases so that the labeled products can be distinguished.

DEFINITIONS

Figure 6:
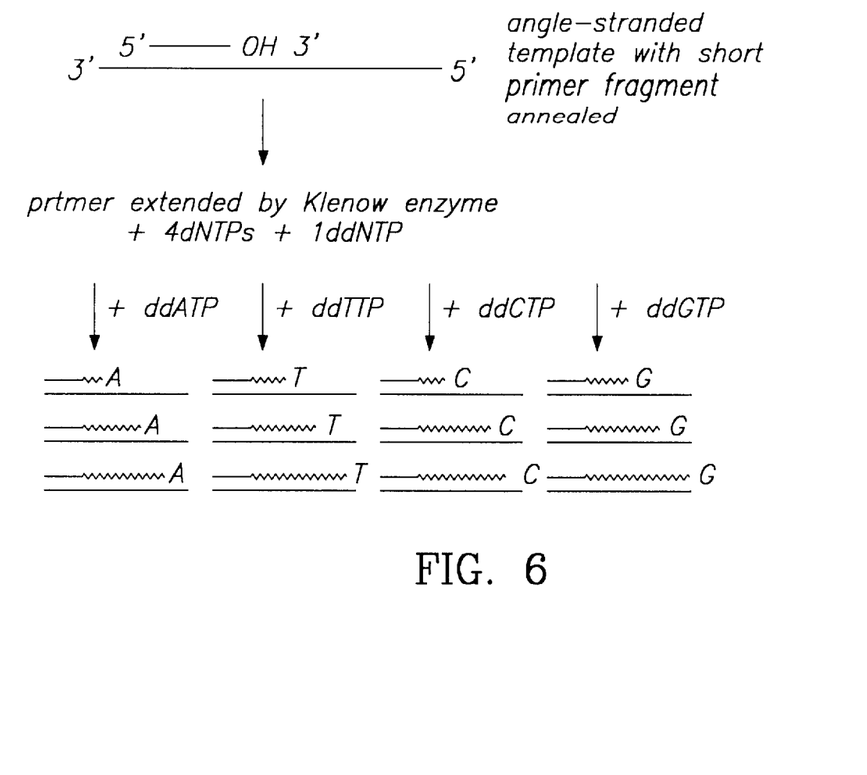
FIG. 6 is a schematic representation of a conventional "Sanger" or "enzymatic sequencing" method.

The term "enzymatic sequencing," "Sanger Method," "dideoxy technique," and "chain terminator technique," are used interchangeably herein to describe a method of sequencing DNA named after its main developer, F. Sanger. The technique uses a single-stranded DNA template, a short DNA primer and a polymerase enzyme to synthesize a complementary DNA strand. The primer is first annealed to the single-stranded template and the reaction mixture is then split into four aliquots and deoxynucleoside triphosphates (dNTPs) plus a dideoxynucleoside triphosphate (ddNTP) are added such that each tube has a different ddNTP. The polymerase will incorporate a ddNTP opposite its complementary base on the template but no further dNTPs can be added as the ddNTP lacks a 3' hydroxyl group. The ratio of ddNTP to dNTP is such that the polymerase will terminate the growing DNA chain at all positions at which the ddNTP can be inserted and so a nested set of fragments (i.e. primer extension products) is formed which all have one end, the primer, in common. The fragments are labeled so that when the four reaction mixtures are electrophoresed through a polyacrylamide gel, a gel band pattern or ladder is formed from which the DNA sequence can be read directly. The process is shown schematically in FIGS. 6 & 7.

The term "labeled" means any detectable label including radioactive, enzyme and fluorescent labels.

The term "enzymatically produced" means produced at least in part as a result of an action of an enzyme, e.g. fragments of nucleotides are produced when an enzyme catalyzes a reaction whereby a larger sequences is cleaved into two or more fragments.

The term "primer" shall mean a polymer sequence which is complementary and capable of hybridizing to some part of a single stranded nucleotide sequence being sequenced which primer is used to initiate DNA synthesis in vitro.

The term "primer extension product" means the polynucleotide fragment comprising the primer sequence and chain terminator which is produced during enzymatic sequencing.

The term "capturable moiety," "capturable chain terminators," and the like are used interchangeably herein to describe a molecular moiety bound to a 3' end of a nucleotide sequence, which moiety is capable of forming a bond with a moiety on a solid phase.

DESCRIPTION OF THE SPECIFIC EMBODIMENTS

Improved methods of determining a nucleic acid sequence through enzymatic sequencing are provided. In the subject methods, primers are used in combination with capturable chain terminators to produce primer extension products capable of being captured on a solid phase, where the primer extension products may be labeled, e.g. by employing labeled primers to generate the primer extension products. Following generation of the primer extension products, the primer extension products are isolated through capture on a solid phase. The isolated primer extension products are then released from the solid phase, size separated and detected to yield sequencing data from which the nucleic acid sequence is determined.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Figure 7:
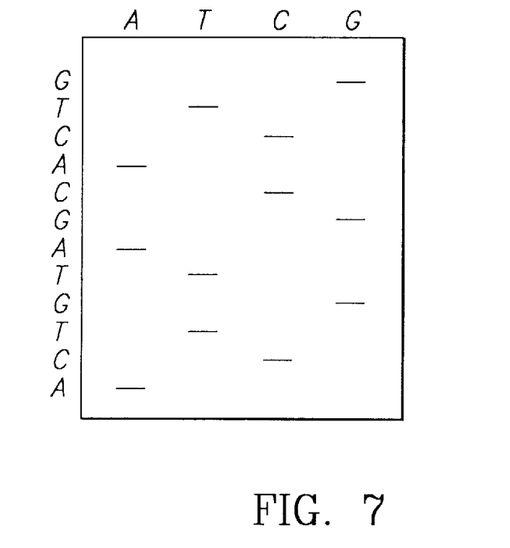
FIG. 7 is a schematic representation of the results obtained using conventional enzymatic sequencing.

Methods of determining the sequence of a nucleic acid, e.g. DNA, by enzymatic sequencing are well known in the art and described in Sambrook et al., Molecular Cloning: A Laboratory Manual (Cold Spring Harbor Laboratory Press, 1989) and Griffin and Griffin, "DNA Sequencings, Recent Innovations and Future Trends," Applied Biochemistry and Biotechnology (1993) 38: 147–159, the disclosures of which are herein incorporated by reference. The Sanger method is shown schematically in FIG. 6. Generally, in enzymatic sequencing methods, which are also referred to as Sanger dideoxy or chain termination methods, differently sized oligonucleotide fragments representing termination at each of the bases of the template DNA are enzymatically produced and then size separated yielding sequencing data from which the sequence of the nucleic acid is determined. The results of such size separations are shown in FIG. 7. The first step in such methods is to produce a family of differently sized oligonucleotides for each of the different bases in the nucleic acid to be sequenced, e.g. for a strand of DNA comprising all four bases (A, G, C, and T) four families of differently sized oligonucleotides are produced, one for each base. See FIG. 6. To produce the family of differently sized oligonucleotides, each base in the sequenced nucleic acid, i.e. template nucleic acid, is combined with an oligonucleotide primer, a polymerase, nucleotides and a dideoxynucleotide corresponding to one of the bases in the template nucleic acid. Each of the families of oligonucleotides are then size separated, e.g. by electrophoresis, and detected to obtain sequencing data, e.g. a separation pattern or electropherogram, from which the nucleic acid sequence is determined. See FIG. 7.

Before further describing the subject methods in greater detail, the critical chain terminator reagents employed in the subject methods will be discussed. Critical to the subject methods is the use of capturable chain terminators to produce the families of different sized oligonucleotide fragments (hereinafter referred to as primer extension products) comprising a capture moiety at the 3' terminus. The primer sequences employed to generate the primer extension products will be sufficiently long to hybridize the nucleic acid comprising the target or template nucleic acid under chain extension conditions, where the length of the primer will generally range from 6 to 40, usually 15 to 30 nucleotides in length. The primer will generally be a synthetic oligonucleotide, analogue or mimetic thereof, e.g. a peptide nucleic acid. Although the primer may hybridize directly to the 3' terminus of the target nucleic acid where a sufficient portion of this terminus of the target nucleic acid is known, conveniently a universal primer may be employed which anneals to a known vector sequence flanking the target sequence. Universal primers which are known in the art and commercially available include pUC/M13, λgt10, λgt11 and the like.

In one preffered embodiment of the subject invention, the primers employed in the subject invention will comprise a detectable label. A variety of labels are known in the art and suitable for use in the subject invention, including radioisotopic, chemiluminescent and fluorescent labels. As the subject methods are particularly suited for use with methods employing automated detection of primer extension products, fluorescent labels are preferred. Fluorescently labeled primers employed in the subject methods will generally comprise at least one fluorescent moiety stably attached to one of the bases of the oligonucleotide.

The primers employed in the subject invention may be labeled with a variety of different fluorescent moieties, where the fluorescer or fluorophore should have a high molar absorbance, where the molar absorbance will generally be at least $10^3 \text{cm}^{-1}\text{M}^{-1}$, usually at least $10^4 \text{cm}^{-1}\text{M}^{-1}$, and preferably at least $10^5 \text{cm}^{-1}\text{M}^{-1}$, and a high fluorescence quantum yield, where the fluorescence quantum yield will generally be at least about 0.1, usually at least about 0.2 and preferably at least about 0.5.

For primers labeled with a single fluorescer, the wavelength of light absorbed by the fluorescer will generally range from about 300 to 900 nm, usually from about 400 to 800 nm, where the absorbance maximum will typically occur at a wavelength ranging from about 500 to 800 nm. Specific fluorescers of interest for use in singly labeled primers include: fluorescein, rhodamine, BODIPY, cyanine dyes and the like, and are further described in Smith et al, Nature (1 986) 321: 647–679, the disclosure of which is herein incorporated by reference.

Of particular interest for use in the subject methods are energy transfer labeled fluorescent primers, in which the primer comprises both a donor and acceptor fluorescer component in energy transfer relationship. Energy transfer labeled primers are described in PCT/US95/01205 and PCT/US96/13134, as well as in Ju et al., Nature Medicine (1996)2: 246–249, the disclosures of which are herein incorporated by reference.

In an alternative embodiment of the subject invention, instead of using labeled primers labeled deoxynucleotides are employed, such as fluorescently labeled dUTP, which are incorporated into the primer extension product resulting in a labeled primer extension product.

The dideoxynucleotides employed as capturable chain terminators in the subject methods will comprise a functionality capable of binding to a functionality present on a solid phase. The bond arising from reaction of the two functionalities should be sufficiently strong so as to be stable under washing conditions and yet be readily disruptable by specific chemical or physical means. Generally, the chain terminator dideoxynucleotide will comprise a member of a specific binding pair which is capable of specifically binding to the other member of the specific binding pair present on the solid phase. Specific binding pairs of interest include ligands and receptors, such as antibodies and antigens, biotin and strept/avidin, sulfide and gold (Cheng & Brajter-Toth, Anal.Chem. (1996)68: 4180–4185, and the like, where either the ligand or the receptor, but usually the ligand, member of the pair will be present on the chain terminator. Of particular interest for use as chain terminators are biotinylated dideoxynucleotides, where such dideoxynucleotides are known in the art and available commercially, e.g. biotin-11-ddATP, biotin-11-ddGTP, biotin-11-ddCTP and biotin-11-ddTTP, and the like.

Turning now to the subject methods, the nucleic acids which are capable of being sequenced by the subject methods are generally deoxyribonucleic acids that have been cloned in appropriate vector, where a variety of vectors are known in the art and commercially available, and include M13mp18, pGEM, pSport and the like. The first step in the subject method is to prepare a reaction mixture for each of the four different bases of the sequence to be sequenced or target DNA. Each of the reaction mixtures comprises an enzymatically generated family of primer extension products, usually labeled primer extension products, terminating in the same base. In other words, in practicing the subject method, one will first generate an "A," "G," "C," and "T," family of differently sized primer extension products using the target DNA as template. To generate the four families of differently sized primer extension products, template DNA, a DNA polymerase, primer (which may be labeled), the four different deoxynucleotides, and capturable dideoxynucleotides are combined in a primer extension reaction mixture. The components are reacted under conditions sufficient to produce primer extension products which are differently sized due to the random incorporation of the capturable dideoxynucleotide and subsequent chain termination. Thus, to generate the "A" family of differently sized primer extension products, the above listed reagents will be combined into a reaction mixture, where the dideoxynucleotide is ddATP modified to comprise a capturable moiety, e.g. biotinylated ddATP, such as biotin-11-ddATP. The remaining "G," "C," and "T" families of differently sized primer extension products will be generated in an analogous manner using the appropriate dideoxynucleotide.

Where labeled primers are employed to generate each of the families of primer extension products, the labeled primers may be the same or different. Preferably, the labeled primer employed will be different for production of each of the four families of primer extension products, where the labels will be capable of being excited at substantially the same wavelength and yet will provide a distinguishable signal. The use of labels with distinguishable signals affords the opportunity of separating the differently sized primer extension products when such products are together in the same separation medium. This results in superior sequencing data and therefore more accurate sequence determination. For example, one can prepare the "A" family of primer extension products with a first fluorescent label capable of excitation at a wavelength from about 470 to 480 nm which fluoresces at 525 nm. The label used in production of "G," "C," and "T" families will be excitable at the same wavelength as that used in the "A" family, but will emit at 555 nm, 580 nm, and 605 nm respectively. Accordingly, the primer extension labels are designed so that all four of the labels absorb at substantially the same wavelength but emit at different wavelengths, where the wavelengths of the emitted light differ in detectable and differentiatable amounts, e.g. differ by at least 15 nm.

The next step in the subject method is isolation of the primer extension products. The primer extension products are isolated by first capturing the primer extension products on a solid phase through the capture moiety at the 3' terminus of the primer extension product and then separating the solid phase from the remaining components of the reaction mixture. Capture of the primer extension products occurs by contacting the reaction mixture comprising the family of primer extension products with a solid phase. The solid phase has a member of a specific binding pair on its surface. The other member of the specific binding pair is bonded to the primer extension products, as described above. Contact will occur under conditions sufficient to provide for stable binding of the specific binding pair members. A variety of different solid-phases are suitable for use in the subject methods, such phases being known in the art and commercially available. Specific solid phases of interest include polystyrene pegs, sheets, beads, magnetic beads, gold surface and the like. The surfaces of such solid phases have been modified to comprise the specific binding pair member, e.g. for biotinylated primer extension products, streptavidin coated magnetic bead may be employed as the solid phase.

Following capture of the primer extension reaction products on the solid phase, the solid phase is then separated from the remaining components of the reaction mixture, such as template DNA, excess primer, excess deoxy- and dideoxynucleotides, polymerase, salts, extension products which do not have the capture moiety, and the like. Separation can be accomplished using any convenient methodology. The methodology will typically comprise washing the solid phase, where further steps can include centrifugation, and the like. The particular method employed to separate the solid-phase is not critical to the subject invention, as long as the method employed does not disrupt the bond linking the primer extension reaction product from the solid-phase.

The primer extension products are then released from the solid phase. The products may be released using any convenient means, including both chemical and physical means, depending on the nature of the bond between the specific binding pair members. For example, where the bond is a biotin-strept/avidin bond, the bond may be disrupted by contacting the solid phase with a chemical disruption agent, such as formamide, and the like, which disrupts the biotin-strept/avidin bond and thereby releases the primer extension product from the solid phase. The released primer extension products are then separated from the solid phase using any convenient means, including elution, centrifugation and the like.

The next step in the subject method is to size separate the primer extension products. Size separation of the primer extension products will generally be accomplished through electrophoresis, in which the primer extension products are moved through a separation medium under the influence of an electric field applied to the medium, as is known in the art. Alternatively, for sequencing with Mass Spectrometry (MS) where unlabeled primer extension products are detected, the sequencing fragments are separated by the time of the flight chamber and detected by the mass of the fragments. See Roskey et al., Proc. Natl. Acad. Sci. USA (1996) 93: 4724–4729. The subject methodology is especially important for obtaining accurate sequencing data with MS, because the subject methodology offers a means to load only the primer extension products terminated with the capturable chain terminators, eliminating all other masses, thereby producing accurate results.

In methods in which the fragments are size separated, the size separated primer extension products are then detected, where detection of the size separated products yields sequencing data from which the sequence of the target or template DNA is determined. For example, where the families of fragments are separated in a traditional slab gel in four separate lanes, one corresponding to each base of the target DNA, sequencing data in the form of a separation pattern is obtained. See FIG. 7. From the separation pattern, the target DNA sequence is then determined, e.g. by reading up the gel. See bases shown on left of FIG. 7. Alternatively, where automated detectors are employed and all of the reaction products are separated in the same electrophoretic medium, the sequencing data may take the form of an electropherogram, as is known in the art, from which the DNA sequence is determined.

Where labeled primers are employed, the nature of the labeled primers will, in part, determine whether the families of labeled primer extension products may be separated in the same electrophoretic medium, e.g. in a single lane of slab gel or in the same capillary, or in different electophoretic media, e.g. in different lanes of a slab gel or in different capillaries. Where the same labeled primer generating the same detectable single is employed to generate the primer extension products in each of the different families, the families of primer extension products will be electrophoretically separated in different electrophoretic media, so that the families of primers extension products corresponding to each base in the nucleic acid can be distinguished.

Where different labeled primers are used for generating each family of primer extension products, the families of products may be grouped together and electrophoretically separated in the same electrophoretic medium. In this preferred method, the families of primer extension products may be combined or pooled together at any convenient point following the primer extension product generation step. Thus, the primer extension products can be pooled either prior to contact with the solid phase, while bound to the solid phase or after separation from the solid phase but prior to electrophoretic separation.

Kits for practicing the subject sequencing methods are also provided. At a minimum such kits will comprise capturable chain terminators, e.g. biotinylated-ddATP; -ddTTP; -ddCTP and -ddGTP. For embodiments in which the primer extension products are labeled, the kits will further comprise a means for generating labeled primer extension products, such as labeled deoxynucleotides, or preferably labeled primers, where the labeled primers are preferably Energy Transfer labeled primers which absorb at the same wavelength and provide distinguishable fluorescent signals. Conveniently, the kits may further comprise one or more additional reagents useful in enzymatic sequencing, such as vector, polymerase, deoxynucleotides, buffers, and the like. The kits may further comprise a plurality of containers, wherein each contain may comprise one or more of the necessary reagents, such as labeled primer, unlabled primer or degenerate primer, dNTPs, dNTPs containing a fraction of fluorescent dNTPs, capturable ddNTP, polymerase and the like. The kits may also further comprise solid phase comprising a moiety capable of binding with the capturable ddNTP, such as streptavidin coated magnetic beads and the like.

The following examples are offered by way of illustration and not by way of limitation. The following examples are put forth so as to provide those of ordinary skill in the art with a complete disclosure and description of how to make and use the subject sets of fluorescent labels.

EXPERIMENTAL

DNA Sequencing procedure.

Sequencing was performed using M13mp18 or pGEM template DNA, energy transfer primers (- 40M 13 forward or -28M 13 reverse (see Vandor Horn et al., Comments (1996) 23,7 (Amersham Life Sciences)) and Thermo Sequenase (from Amersham Life Sciences) on an ABI 377 sequencer (from Applied Biosystems). Biotin-terminators (BIOTIN-111-ddATP, ddGTP, ddTTP and ddCTP) were obtained from NEN Life Science (Boston, Mass.). Four reactions were run, one for each dye/ddNTP combination. The reactions containing ddCTP were run with the F10F primer, ddATP with the F10G primer, ddGTP with the F10T primer, and ddTTP with the F10R primer, where these specific primers are disclosed in Vander Horn et al., supra. For A and G reactions, 1.6 μl of dNTP/ddNTP mix (700 mM each of 7-deaza-dGTP, dATP, dTTP and dCTP with 2.5 μM of the BIOTIN-11-ddATP or BIOTIN-11-ddGTP) were mixed with 0.4 μl of reaction buffer (260 mM Tris/HCl pH 9.5, 65 mM $MgCl_2$), 0.2 pmol of primer, 1.0 μl of Thermo Sequenase (1.7 U/μl) and 2 μl of DNA template. For T and C reactions, 3.2 μl of dNTP/ddNTP mix (613 mM each of 7-deaza-dGTP, dATP, dTTP and dCTP with 2.5 μM of the BIOTIN-11-ddTTP or BIOTIN-11-ddCTP) were mixed with 0.8 μl of reaction buffer (260 mM Tris/HCl pH 9.5, 65 mM $MgCl_2$), 0.4 pmol of primer, 2.0 μl of Thermo Sequenase (1.7 U/μl) and 4 μl of DNA template. Thirty one cycles of 96° C. for 20 seconds, 50° C. for 20 seconds and 60° C. for 3 minutes were carried out on the sequencing sample. The four reaction mixtures for each sequence were then stopped by adding 4 μl of 10×TE buffer and combined into one vial.

Solid-Phase purification procedure.

80 μl of streptavidin coated magnetic beads (Dynabeads M-280) were washed with 2×80 μl binding and washing (B&W) buffer (10 mM Tris-HCl, pH 7.5, 1 mM EDTA and 2.0M NaCl) and then resuspended in 50 μl of B&W buffer. The entire sequencing reaction mixtures were combined with 50 μl of the streptavidin coated magnetic beads (from Dyanl) and incubated at 50° C. for one hour with occasional mixing. The supernatant was removed while the magnetic beads were immobilized with a magnet. The beads were then washed twice with 2×100 μl of B&W buffer, once with 100 μl 1×TE and once with 100 μl of deionized water. The biotinylated sequencing DNA fragments were eluted from the magnetic beads in 6 μl of formamide containing 10 mM EDTA at 94° C. for 5 min and 1 μl of supernatant was loaded on a 4% polyacrylamide 7M urea denaturing gel mounted in the 377 instrument. Electrophoresis was conducted with 48 A run module for 10 hours using 1×TBE buffer with an ABI 377 DNA sequencer.

Figure 5A:
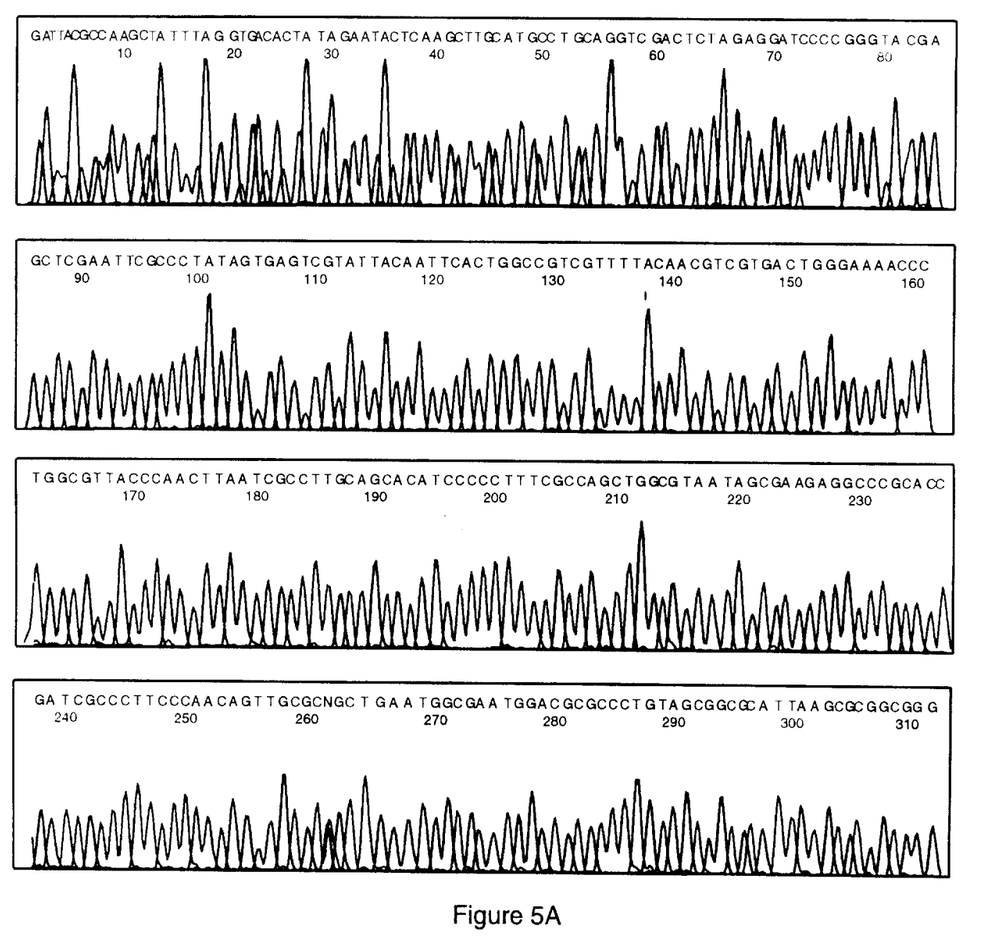
FIG. 5 shows a complete electropherogram of a four color sequencing sample (pGEM) generated with biotin-terminators after purification with streptavidin coated magnetic beads. The data are essentially free of noise. Good sequences are obtained up to 800 bp.
Figure 5B:
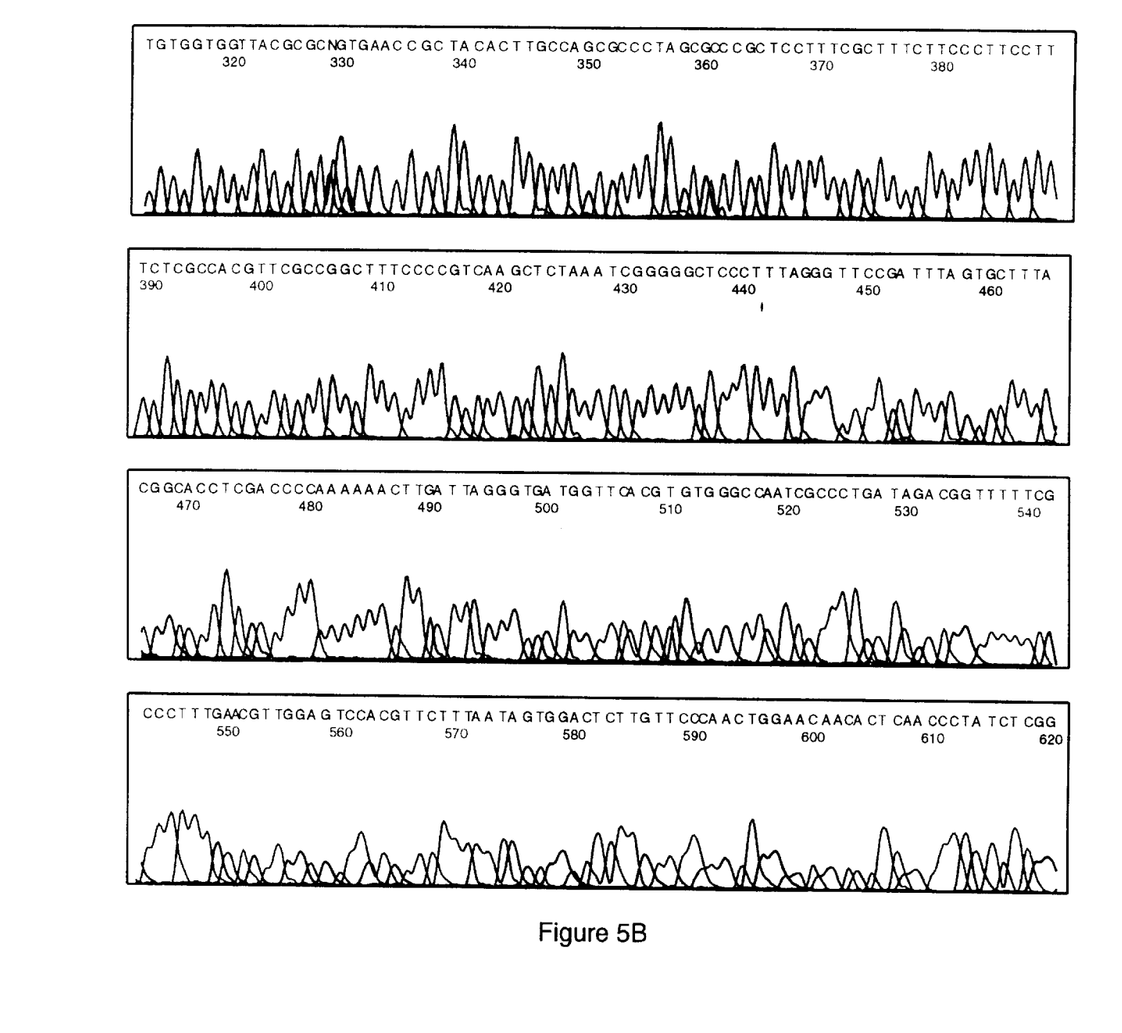
Figure 5C:
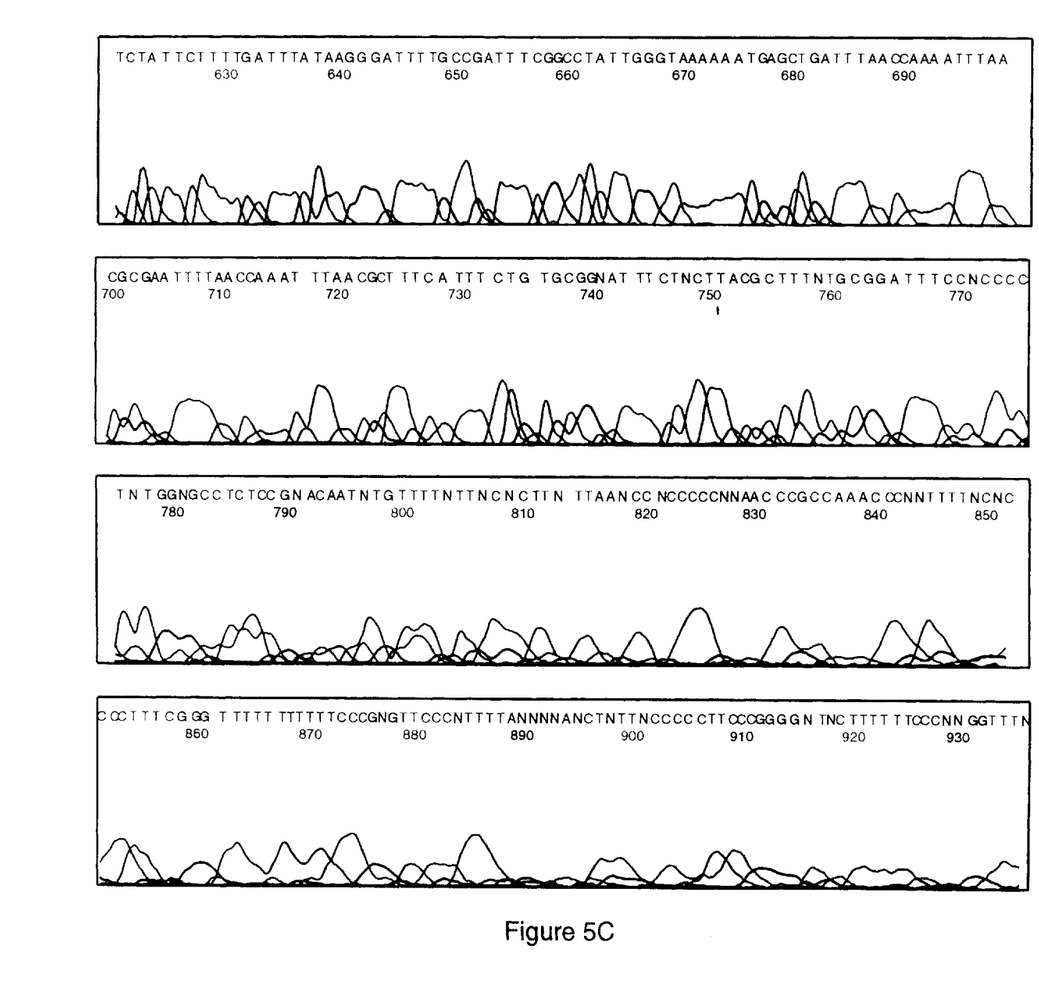

Results. FIG. 5 shows a complete electropherogram of a four color sequencing sample of (pGEM) generated with biotin-terminators after purification with streptavidin coated magnetic beads according to the methods described above. The data are essentially free of noise. Good sequences are obtained up to 800 bp. Similar results were obtained with other templates.

Comparative Results.

Figure 1:
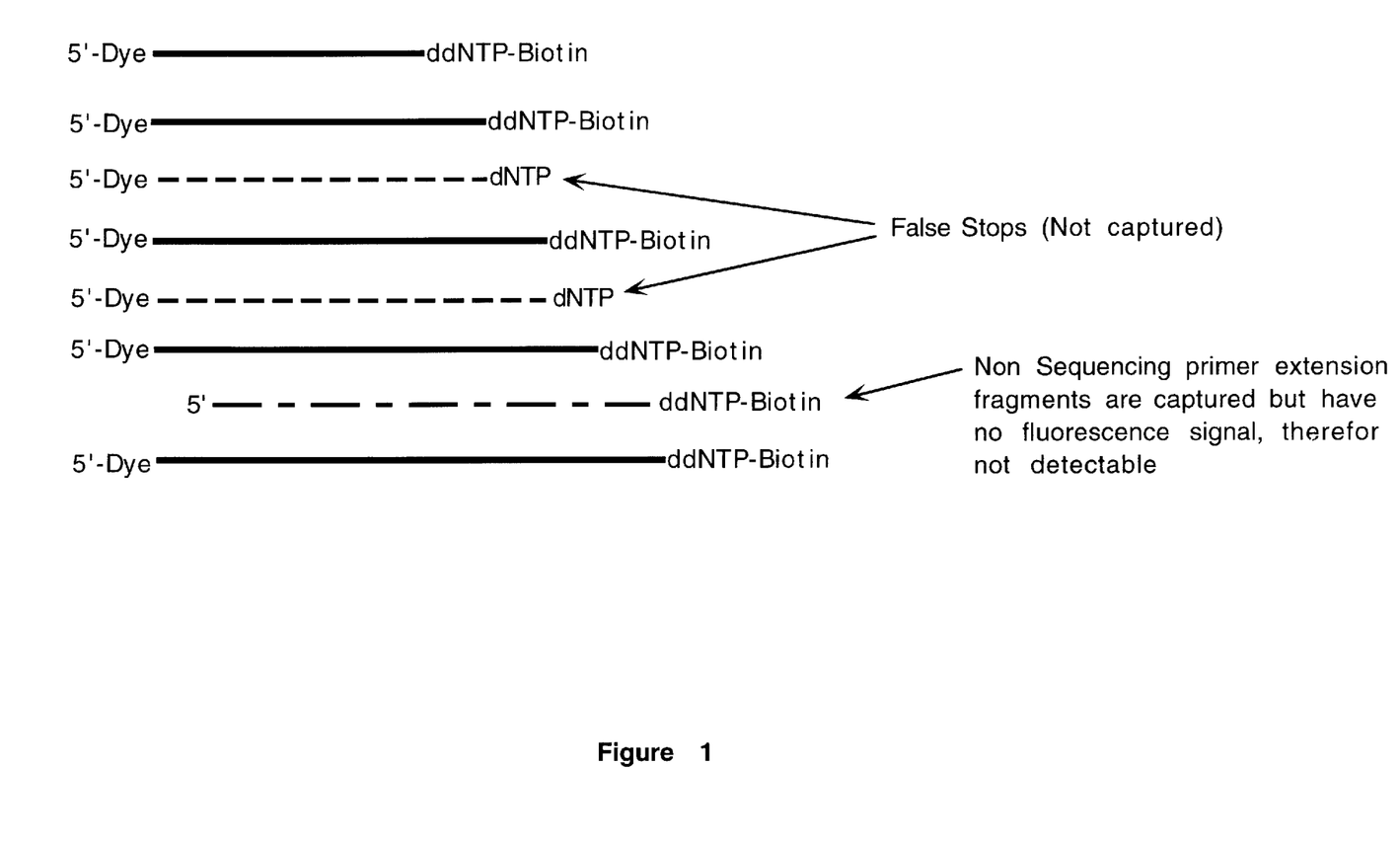
FIG. 1 is a schematic representation demonstrating that when dye labeled primers and biotin-terminators are employed to generate sequence fragments followed by subsequent isolation of the sequencing fragments with streptavidin coated magnetic beads, only true sequencing fragments are detected in the fluorescence DNA sequencer. False stopped fragments are not captured and non sequencing primer extension fragments resulting from RNA and nicked DNA fragments are not detected.
Figure 2:
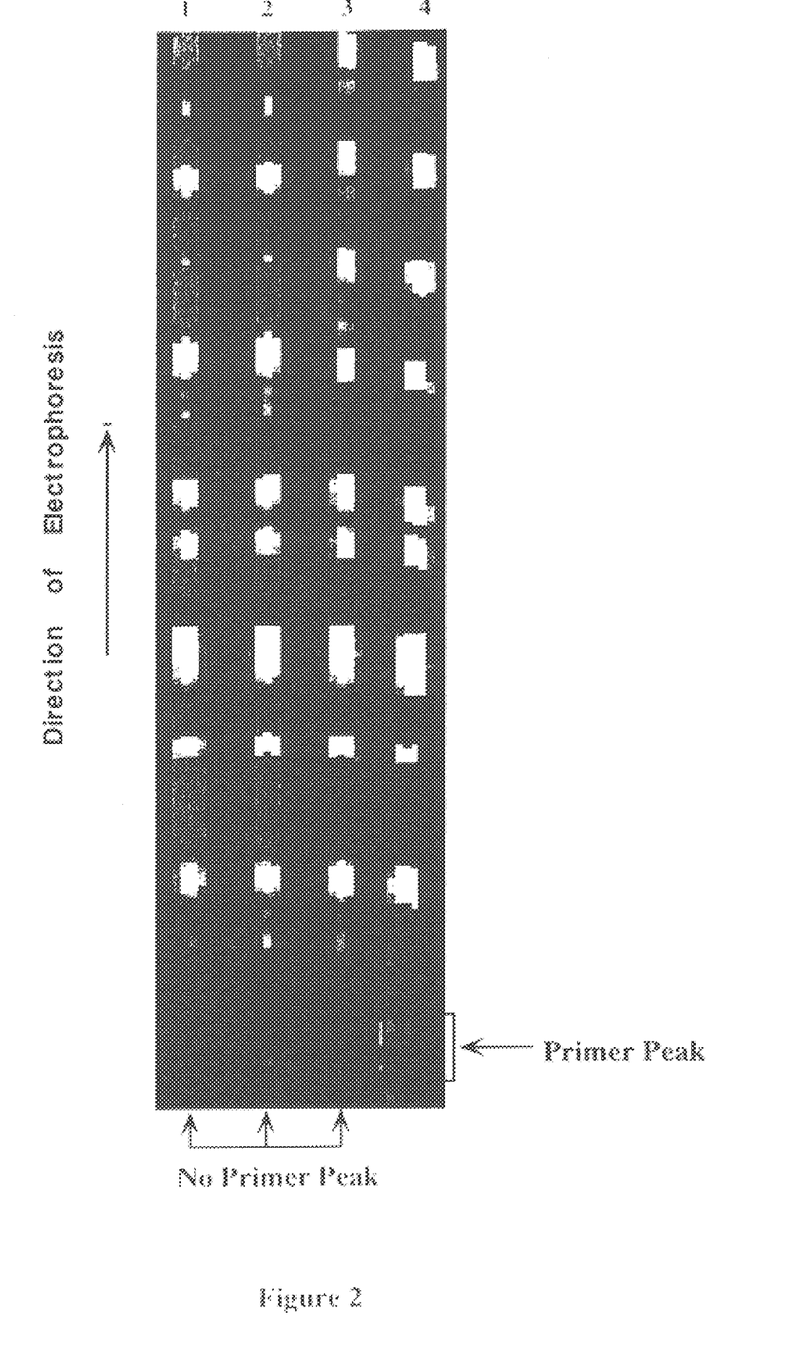
FIG. 2 shows a portion of a sequencing gel image of four sequencing samples generated with biotin-terminators. Sample 1–3 were purified by streptavidin coated magnetic beads which eliminate the primer peaks completely. Sample 4 was purified by ethanol precipitation which leaves a large primer peak.

To compare the results obtainable with the present methods to those obtainable with ethanol precipitation, four sequencing samples were generated using biotin terminators. 3 of the sequencing samples were purified using streptavidin coated beads, while the remaining sample was subject to ethanol precipitation. FIG. 2 shows a portion of a sequencing gel image of the four sequencing samples generated with biotin-terminators. Sample 1–3 were purified by streptavidin coated magnetic beads which eliminate the primer peaks completely. Sample 4 was purified by ethanol precipitation which leaves a large primer peak.

Figure 3A:
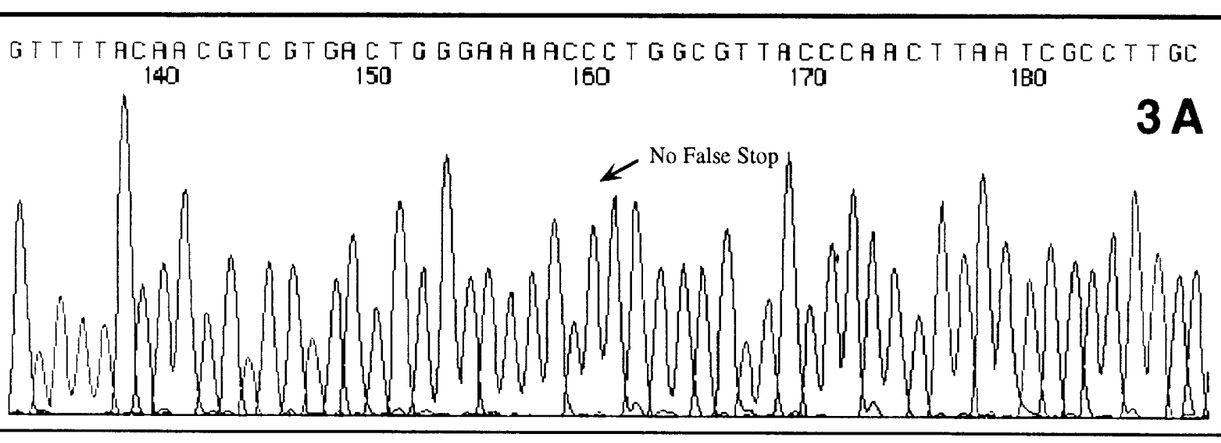
FIGS. 3A and 3B show that the four color sequencing data generated with biotinterminators and energy transfer (ET) primers after purification with streptavidin coated magnetic beads (A) are much cleaner than the sequencing data generated with ET primer and regular ddNTPs (B). A false stop peak in B resulted in a sequence error. In the same sequence region no false peak was seen in A.
Figure 3B:
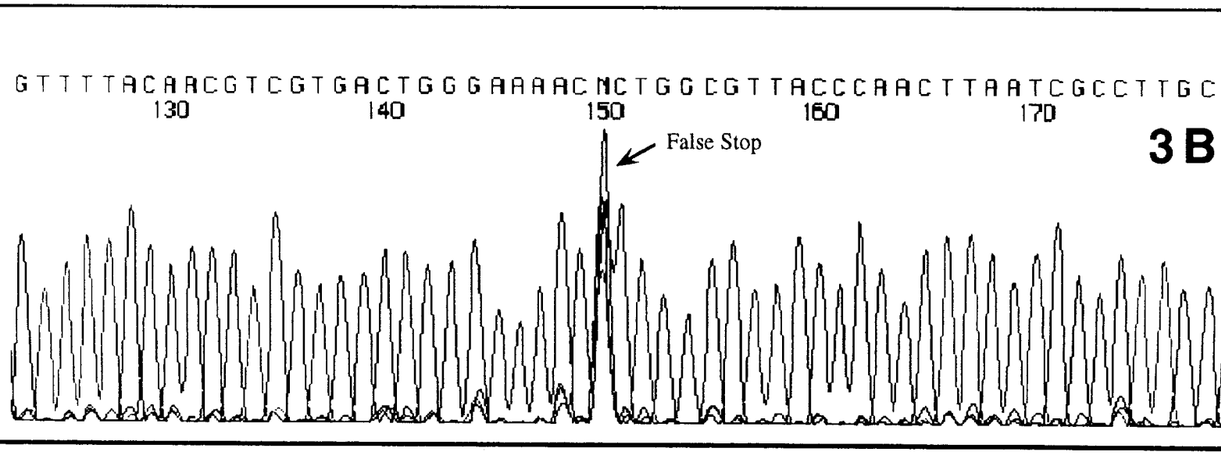
Figure 4A:
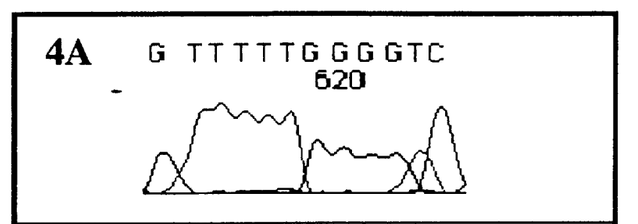
FIGS. 4A and 4B show that the resolution of the four color sequencing data generated with biotin-terminators and ET primers after purification with streptavidin coated magnetic beads (A) are better than the same sequencing sample purified only by ethanol precipitation (B).
Figure 4B:
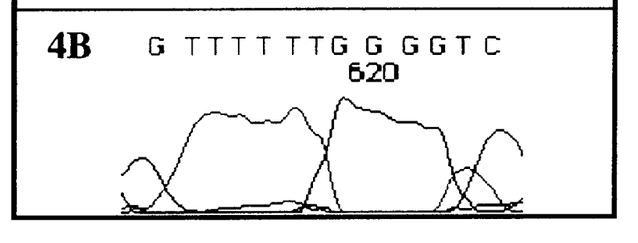

Sequencing fragments were produced using M13mp18 and pGEM as template and four color energy transfer primers (M13-40, F10F, F10G, F10T, F10R). In one set (A) biotin terminators were employed, while in the other set (B) regular non-biotinylated terminators were employed. The sequencing fragments of set A were subjected to purification using streptavidin coated magnetic beads, while the fragments of set B were not. FIG. 3 shows that the four color sequencing data generated with biotin-terminators and energy transfer (ET) primers after purification with streptavidin coated magnetic beads (A) are much cleaner than the sequencing data generated with ET primer and regular ddNTPs (B). A false stop peak in B resulted in a sequence error. In the same sequence region no false peak was seen in A. FIG. 4 shows that the resolution of the four color sequencing data generated with biotin-terminators and ET primers after purification with streptavidin coated magnetic beads (A) are better than the same sequencing sample purified only by ethanol precipitation (B).

The above results and discussion demonstrate that by employing labeled primers and solid phase capturable chain terminators in enzymatic sequencing methods, highly accurate sequence data can be obtained, even for long DNA strands. By using the subject methods, only the true DNA sequencing fragments are isolated and detected, as the subject methods eliminate background because of false stops, self priming RNA, and nicked double stranded DNA. Furthermore, by using the subject methods, salts, excess primer, template nucleic acid and other reagents necessary for generation of the sequencing fragments are separated from the sequencing fragments prior to detection and isolation, resulting in improved results.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining the sequence of a nucleic acid, said method comprising:

(a) preparing a reaction mixture corresponding to each base of said nucleic acid, wherein each of said reaction mixtures comprises a family of enzymatically produced capturable primer extension products produced by combining said nucleic acid, polymerase, deoxynucleotides, oligonucleotide primer and capturable dideoxy chain terminator in a reaction mixture under conditions sufficient to produce said capturable primer extension products;

(b) contacting each of said reaction mixtures with a solid phase capable of capturing said primer extension products comprising said capturable chain terminator through interaction of moities present on said solid phase and said chain terminator to produce solid phase captured primer extension products;

(c) separating said solid phase captured primer extension products from said reaction mixture;

(d) releasing said primer extension products from said solid phase;

(e) size separating and detecting said released primer extension products to produce sequencing data; and (f) determining the sequence of said nucleic acid from said sequencing data.

2. The method according to claim 1, wherein said primer extension products are labeled.

3. The method according to claim 2, wherein said oligonucleotide primer used to prepare said labeled primer extension products is labeled.

4. The method according to claim 2, wherein said released primer extension products from each of said reaction mixtures are size separated in different electrophoretic media and said sequencing data is a separation pattern.

5. The method according to claim 4, wherein said different electrophoretic media are adjacent lanes in a slab gel.

6. The method according to claim 4, wherein said different electrophoretic media are present in different capillaries.

7. The method according to claim 4, wherein the labeled primer extension products from each of said reaction mixtures comprise the same label.

8. The method according to claim 2, wherein said released primer extension products from each of said reaction mixtures are size separated in the same electrophoretic medium.

9. The method according to claim 3, wherein said labeled oligonucleotide primer is fluorescently labeled and said sequencing data is an electropherogram.

10. The method according to claim 2, wherein the labels of the labeled primer extension products in each reaction mixture are excited at substantially the same wavelength and provide distinguishable signals.

11. The method according to claim 1, wherein said primer extension products are unlabled and said sequence is determined by mass spectrometry.

12. A method of determining the sequence of a DNA, said method comprising:

(a) preparing four different reaction mixtures corresponding to each base of said nucleic acid, wherein each of said reaction mixtures comprises a family of enzymatically produced fluorescently labeled primer extension products comprising a first member of a specific binding pair produced by combining said nucleic acid, polymerase, deoxynucleotides, fluorescently labeled oligonucleotide primer and dideoxynucleotide bonded to said first member of a specific binding pair member;

(b) contacting each of said reaction mixtures with a solid phase comprising a second member of said specific binding pair whereby said first and second members bind and solid phase captured fluorescently labeled primer extension products are produced;

(c) separating said solid phase captured fluorescently labeled primer extension products from said reaction mixture;

(d) releasing said captured fluorescently labeled primer extension products from said solid phase;

(e) size separating and detecting said released fluorescently labeled primer extension products to produce an electropherogram; and (f) determining the sequence of said nucleic acid from said electropherogram.

13. The method according to claim 12, wherein said fluorescently labeled primer extension products from each of said four reaction mixtures are pooled prior to step (e).

14. The method according to claim 13, wherein said four reaction mixtures are pooled prior to step (b).

15. The method according to claim 13, wherein said four reaction mixtures are pooled prior to step (d).

16. The method according to claim 12, wherein said first member of a specific binding pair is biotin.

17. The method according to claim 12, wherein said second member of a specific binding pair is streptavidin.

18. A method of determining the sequence of a DNA, said method comprising:

(a) preparing a first reaction mixture comprising enzymatically produced fluorescently labeled solid phase capturable primer extension products terminating in "A," wherein said first reaction mixture is prepared by combining said DNA with DNA polymerase, dATP, dGTP, dCTP, dTTP, energy transfer labeled oligonucleotide primer and biotinylated ddATP;

(b) preparing a second reaction mixture comprising enzymatically produced fluorescently labeled solid phase capturable primer extension products terminating in "G" wherein said second reaction mixture is prepared by combining said DNA with DNA polymerase, dATP, dGTP, dCTP, dTTP, energy transfer labeled oligonucleotide primer and biotinylated ddGTP;

(c) preparing a third reaction mixture comprising enzymatically produced fluorescently labeled solid phase capturable primer extension products terminating in "C," wherein said third reaction mixture is prepared by combining said DNA with DNA polymerase, dATP, dGTP, dCTP, dTTP, energy transfer labeled oligonucleotide primer and biotinylated ddCTP;

(d) preparing a fourth reaction mixture comprising enzymatically produced fluorescently labeled solid phase capturable primer extension products terminating in "T," wherein said first reaction mixture is prepared by combining said DNA with DNA polymerase, dATP, dGTP, dCTP, dTTP, energy transfer labeled oligonucleotide primer and biotinylated ddTTP;

(e) pooling said first, second, third and fourth reaction mixtures into a single reaction mixture;

(f) contacting said reaction mixture with a solid phase comprising streptavidin to produce captured fluorescently labeled primer extension products;

(g) separating said captured fluorescently labeled primer extension products from said reaction mixture;

(h) releasing said captured fluorescently labeled primer extension products from said solid phase;

(i) electrophoretically size separating said released fluorescently labeled primer extension products;

(j) irradiating said size separated fluorescently labeled primer extension products;

(k) detecting light emitted from said irradiated fluorescently labeled primer extension products;

(l) producing an electropherogram from said detected light; and (m) determining the sequence of said DNA from said electropherogram.

19. A labeled primer extension product as produced in claim 2, said product comprising a detectable label and a 3' terminal dideoxy chain terminator comprising a capturable moiety.

20. The primer extension product according to claim 19, wherein said primer extension product comprises labeled primer.

21. The primer extension product according to claim 19, wherein said primer extension product is internally labeled.

22. The primer extension product according to claim 19, wherein said 5' terminus is labeled with a fluorescent label.

23. The primer extension product according to claim 20, wherein said labeled primer comprises an energy transfer label.

24. The primer extension product according to claim 19, wherein said capturable moiety is a member of a specific binding pair.

25. The primer extension product according to claim 24, wherein said specific binding pair consists of biotin and streptavidin.

26. A kit for use in determining the sequence a nucleic acid, said kit comprising:
   at least one of labeled oligonucleotide primer and labeled dNTPs; and
   solid phase capturable chain terminator.

27. The kit according to claim 26, wherein said kit comprises at least one of four distinguishably labeled oligonucleotide primers and four distinguishably labeled dNTPs.

28. The kit according to claim 26, wherein said labeled oligonucleotide primers are fluorescently labeled.

29. The kit according to claim 26, wherein said solid phase capturable chain terminator is a dideoxynucleotide bonded to a member of a specific binding pair.

30. The kit according to claim 29, wherein said specific binding pair consists of biotin and streptavidin.

31. The kit according to claim 30, wherein said member is biotin.

32. A kit for use in determining the sequence a nucleic acid, said kit comprising:
   a plurality of distinguishably labeled oligonucleotide primers;
   a plurality of containers;
   solid phase capturable chain terminator; and
   a solid phase capable of capturing said chain terminator.

33. The kit according to claim 32, wherein said distinguishably labeled oligonucleotide primers comprise energy transfer labels capable of excitation at a common wavelength.

34. The kit according to claim 32, wherein said solid phase comprises magnetic beads.

* * * * *

UNITED STATES PATENT AND TRADEMARK OFFICE
CERTIFICATE OF CORRECTION

PATENT NO. : 5,876,936
DATED : March 2, 1999
INVENTOR(S) : Jingyue Ju

It is certified that error appears in the above-identified patent and that said Letters Patent is hereby corrected as shown below:

Col. 13, line 14, delete "sequence a" and insert --sequence of a--.
Col. 14, line 9, delete "sequence a" and insert --sequence of a--.

Signed and Sealed this

Fifteenth Day of August, 2000

Attest:

Q. TODD DICKINSON

*Attesting Officer*  *Director of Patents and Trademarks*